United States Patent [19]
Howells

[11] Patent Number: 5,267,490
[45] Date of Patent: Dec. 7, 1993

[54] SAMPLING APPARATUS FOR CRYOGENIC FOOD FREEZERS

[75] Inventor: Roger A. Howells, Orfield, Pa.

[73] Assignee: Air Products and Chemicals, Inc., Allentown, Pa.

[21] Appl. No.: 911,843

[22] Filed: Jul. 10, 1992

[51] Int. Cl.5 .......................... F25D 17/02; G01N 7/00
[52] U.S. Cl. ...................... 73/863.52; 62/64; 62/65; 62/125; 62/374
[58] Field of Search ............... 62/63, 64, 65, 125, 62/127, 374, 380; 73/863.51–863.55

[56] References Cited

U.S. PATENT DOCUMENTS

| | | | |
|---|---|---|---|
| 2,263,452 | 11/1941 | Birdseye | 62/65 X |
| 2,727,390 | 12/1955 | Houston et al. | 73/863.53 |
| 3,485,055 | 12/1969 | Webster et al. | 62/63 |
| 3,498,069 | 3/1970 | Waldin | 62/125 X |
| 3,603,243 | 9/1971 | Foster | 62/374 X |
| 4,403,479 | 9/1983 | Rasovich | 62/374 X |
| 4,788,017 | 11/1988 | Schlomer et al. | 62/63 X |
| 4,843,840 | 7/1989 | Gibson | 62/64 X |
| 4,852,358 | 8/1989 | Acharya et al. | 62/374 X |
| 4,858,445 | 8/1989 | Rasovich | 62/374 |
| 4,966,003 | 10/1090 | Shima | 62/125 X |

OTHER PUBLICATIONS

"Automated Sampling", Sep. 1966, vol. 3, No. 2.

*Primary Examiner*—Henry A. Bennet
*Assistant Examiner*—Christopher B. Kilner
*Attorney, Agent, or Firm*—James C. Simmons; William F. Marsh

[57] ABSTRACT

Sampling device removably mounted proximate the discharge opening in an immersion freezer to collect samples of frozen product as they exit the immersion freezer conveyor and are deposited into a second freezing or equilibrating device.

2 Claims, 2 Drawing Sheets

SAMPLING APPARATUS FOR CRYOGENIC FOOD FREEZERS

FIELD OF THE INVENTION

The present invention pertains to safe removal of product samples from an immersion-type freezer at the discharge roller.

BACKGROUND OF THE INVENTION

Immersion-type cryogenic freezers are used for processing food products to individually freeze things such as shrimp and the like. Immersion-type freezers are sometimes mated to a tunnel freezer so that initial freezing takes place by dipping the product, e.g. shrimp, into a bath of liquid cryogen, removing the product from the bath and conveying to a freezing or equilibrating apparatus, e.g. a tunnel freezer where the vaporized cryogen is used to final freeze the product after initial crust freezing. Air Products and Chemicals, Inc. of Allentown, Pa. sells such freezers with the immersion part being identified as a CRYODIP freezer and the tunnel portion being identified as a CRYOQUICK freezer.

One of the problems with using the combination of the immersion and an after treatment apparatus is the sampling of product as it exits the immersion freezer to determine the degree of freezing so that the speed of passage through the apparatus and other parameters of the said apparatus can be adjusted. Normally to take a sample the immersion freezer must be opened exposing the sample taker to the liquid cryogen, and cryogen vapors which in the case of the cryogen being liquid nitrogen can be potentially harmful to the worker and also result in upsetting the entire freezing process.

BRIEF SUMMARY OF THE INVENTION

The present invention includes a sample access port and sample device placed in the immersion freezer proximate the discharge roller, e.g. where the conveyor reverses direction and where the product falls from the immersion freezer conveyor onto the tunnel freezer conveyor so that the samples can be withdrawn without opening the immersion portion of the freezing system.

DETAILED DESCRIPTION OF THE INVENTION

Figure 1:
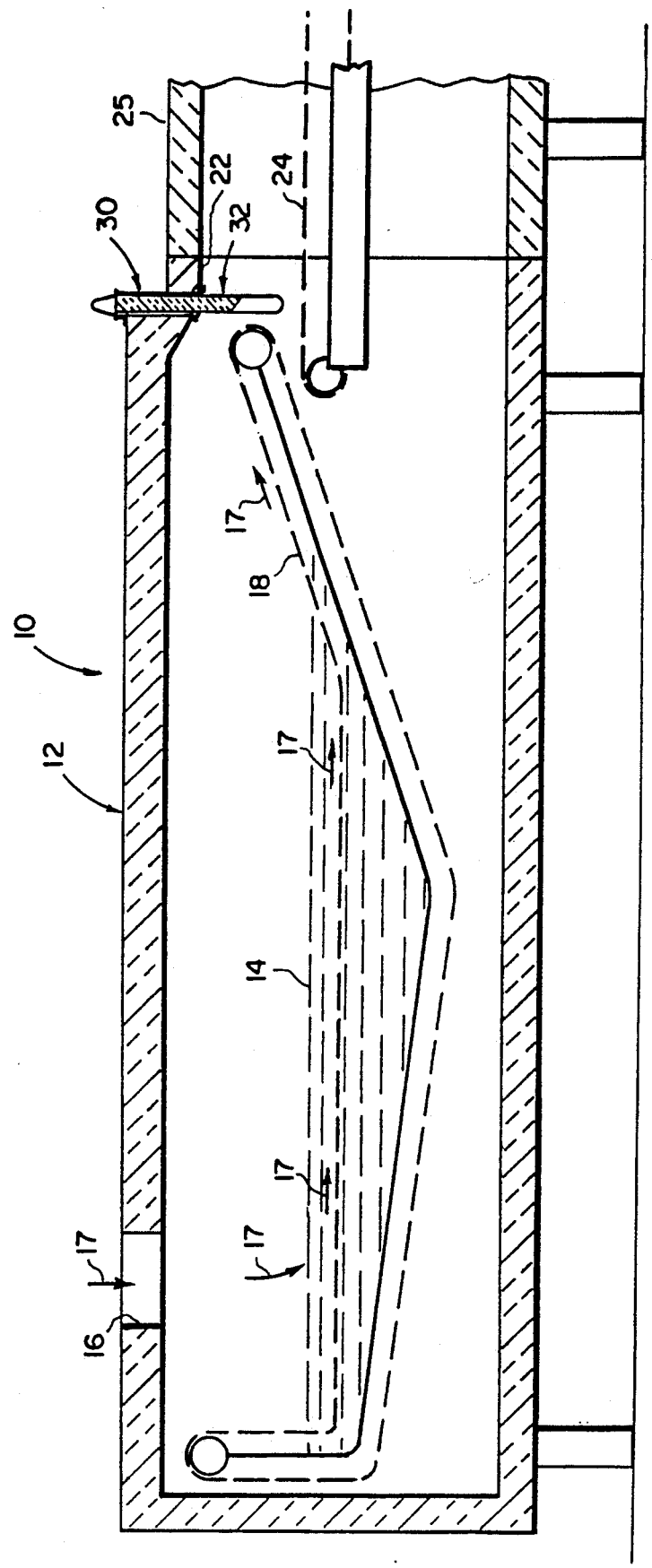
FIG. 1 is a longitudinal schematic of an immersion freezer with the apparatus of the present invention installed.

Referring to FIG. 1, 10 designates an immersion-type cryogenic freezer. Freezer 10 includes housing 12 adapted to contain a bath of liquid cryogen, e.g. liquid nitrogen shown as 14. Housing 12 of freezer 10 that is made in the form of an insulated container. Housing 12 can be made into a single bottom section and a multiple opening top section or can be made in two parts, top and bottom, that can be opened for cleaning as is well known in the art. Product to be frozen is introduced through a product entry port 16 as shown by arrows 17. The product drops into the freezer into the liquid bath and is conducted by a conveyor 18 through the bath and then outwardly through a discharge opening 22 in the housing 14. Normally the conveyor 18 is inclined so that the product 17 emerges from the bath so that residual liquid can drain back into the bath and is not conveyed out of the freezer 10. The product is discharged from conveyor 18 onto a second conveyor 24 which is shown as part of any other type of freezer or temperature equilibrating apparatus 25 to which the immersion freezer can be mated as is well known in the art.

In view of the fact that the operator of such a combined immersion and equilibrating freezing device needs to adjust the freezing parameters based upon the depth of freezing of the product in the immersion section of the process in freezer 10, it is necessary for samples to be taken as they exit the conveyor 18 from the immersion freezer 10. In the past this has been done by opening the immersion freezer 10, thus exposing the person collecting samples to the liquid cryogen, vaporizing cryogen and upsetting the entire freezing process. It has also been possible in those freezers where there is an exhaust duct at the exit end of the immersion freezer to open a clean-out door on the exhaust and take samples in that manner. In other installations it is possible to open the covers of the after treatment apparatus adjacent to the immersion freezer exit with the same resultant exposure to the liquid and gaseous cryogen.

Figure 2:
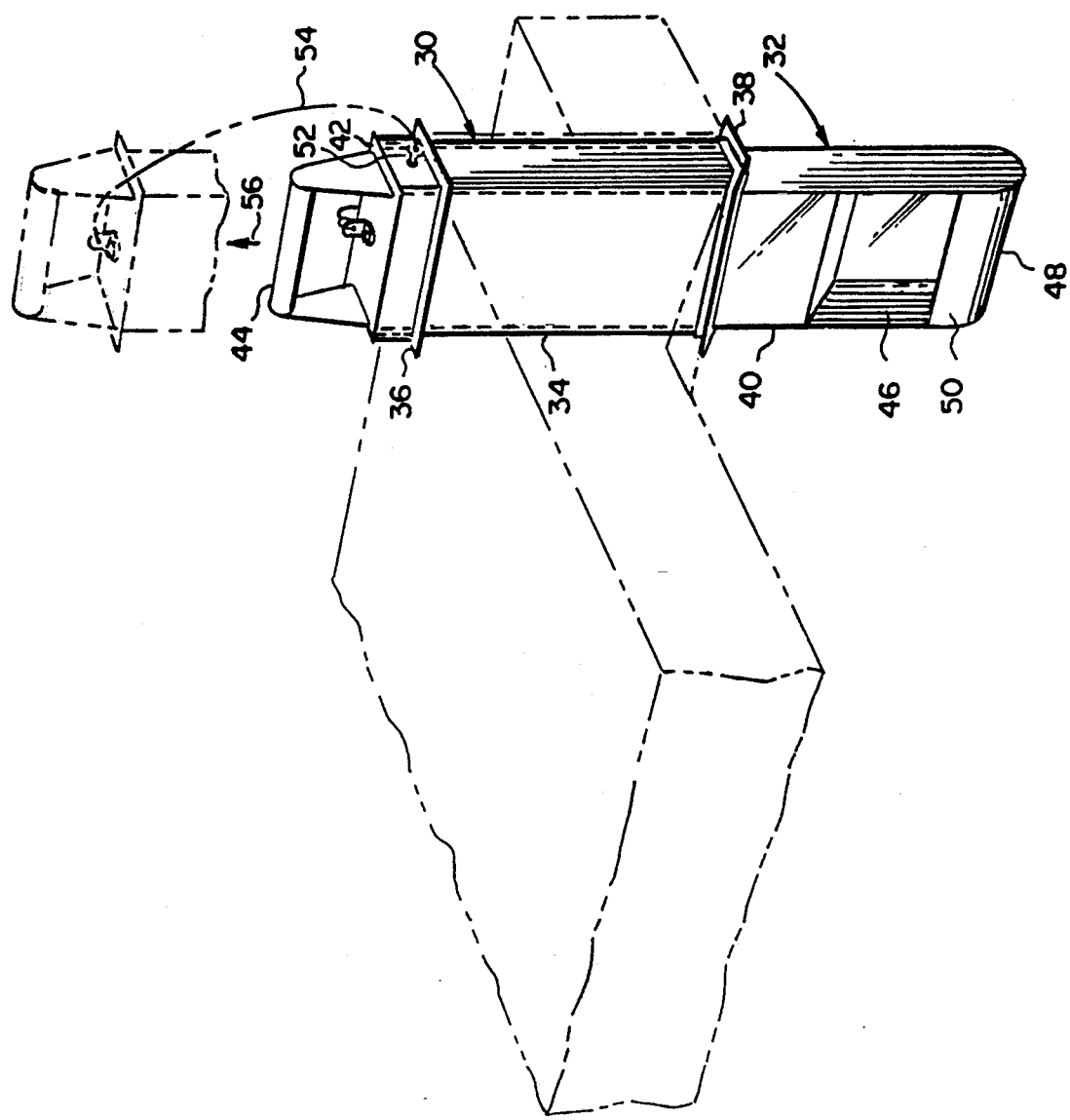
FIG. 2 is an isometric view of the sample collector according to the present invention.

It has been discovered that a safe method of sampling involves installation of a sample port 30 and sample collector 32 as shown in FIGS. 1 and 2. The sample port FIG. 2 includes a generally rectangular shaped body 34 and a top flange 36 and a bottom flange 38, the flanges 36, 38 being adapted to fix the port 30 into the top of the freezer as shown in FIG. 2. The bottom flange 38 is placed onto the port after it is installed in the freezer 10 through a suitably prepared aperture. The entire port 30 can be welded into place or otherwise fastened to the top of the freezer 10 as is well known in the art. Slidably disposed within the port 30 is the sample collector 32 which is in the form of an elongated box 40 having a flange 42 and a handle 44 so that the sample collector 32 can be slideably inserted inside of the port 30 as shown in FIG. 2. Sample collector 32 includes in the housing a large aperture 46 disposed proximate the end 48 of the sample collector that is inserted into the freezer 10. The aperture 46 is fabricated above the end 48 of the sample collector 32 housing 40 so that a dam 50 is created and thus a pocket in the bottom of the sample collector 32.

In use sample collector 32 is introduced into the port 30 so that the aperture 46 faces the conveyor 18 and is disposed with the bottom 48 below the reversing roller 19 of the conveyor 18 so that product 17 falling from conveyor 18 to conveyor 24 will be trapped in the pocket created by the dam 50 of sample collector 32. Sample collector 32 can be quickly removed from the freezer and the samples checked for degree of freezing as shown by the arrow 56 and ghost image in FIG. 2. A pin 52 and wire layer 54 are included for positioning sample collector at the proper position inside freezer 10 in the up or out of service position to block the sample port to prevent air from entering or cold cryogen gas to escape from the freezing apparatus.

Using a device according to the present invention permits the operator to collect samples without opening the freezer, without coming in contact with the liquid cryogen, without being exposed to vaporize liquid cryogen and without upsetting the freezing parameters of the entire system.

Having thus described my invention what is desired to be secured by Letters Patent of the United States is set forth in the appended claims.

I claim:

1. In an immersion freezer of the type having an insulated housing with closed top and bottom sections, a product entry port and a product discharge port, a bath of liquid cryogen maintained in said bottom section and a conveyor to move product dropped into said bath from proximate said entry port to said discharge port by inclining at first that portion of the conveyor proximate the discharge port, the improvement comprising:

an access port in said top section proximate the location of the freezer where said conveyor reverses direction for return to convey more product through said bath; and a sample collector being in the form of an elongated box having a generally rectangular cross-section with an opening in an elongated wide face of the box to intercept product sample, said opening, having a generally rectangular shape disposed above an end of said collector thereby forming a dam over which samples drop into said collector and are retained by the pocket formed in said collector removably disposed in said port, said sample collector so constructed and arranged to be introduced into said freezer through said access port and extended to below the level of said conveyor to intercept samples of product through said opening as they fall off said conveyor, rapid withdrawal of said sample collector permitting a user to quickly and safely test the degree of freezing of product moving through said freezer.

2. A freezer according to claim 1 wherein said access port includes an insulated cover.

* * * * *